United States Patent
Xu et al.

(10) Patent No.: US 11,963,672 B2
(45) Date of Patent: Apr. 23, 2024

(54) ENDOSCOPIC SNARE WITH ASYMMETRIC CORNERS

(71) Applicant: Endo-Therapeutics, Inc., Clearwater, FL (US)

(72) Inventors: Ruijiao Xu, Clearwater, FL (US); Charles Stoddard, Clearwater, FL (US)

(73) Assignee: Endo-Therapeutics, Inc., Clearwater, FL (US)

( * ) Notice: Subject to any disclaimer, the term of this patent is extended or adjusted under 35 U.S.C. 154(b) by 0 days.

(21) Appl. No.: 17/893,788

(22) Filed: Aug. 23, 2022

(65) Prior Publication Data
US 2022/0401089 A1    Dec. 22, 2022

Related U.S. Application Data

(63) Continuation of application No. 16/630,099, filed as application No. PCT/US2018/041872 on Jul. 12, 2018, now Pat. No. 11,439,375.

(60) Provisional application No. 62/531,470, filed on Jul. 12, 2017.

(51) Int. Cl.
*A61B 17/221*  (2006.01)
*A61B 17/00*   (2006.01)

(52) U.S. Cl.
CPC .......... *A61B 17/00234* (2013.01); *A61B 2017/00358* (2013.01); *A61B 2017/00862* (2013.01); *A61B 2017/00867* (2013.01); *A61B 2017/2212* (2013.01)

(58) Field of Classification Search
CPC .......... A61B 17/221; A61B 17/32056; A61B 2017/00287; A61B 2017/00358; A61B 2017/22035; A61B 2017/2212; A61B 2018/1407; A61B 2018/141
See application file for complete search history.

(56) References Cited

U.S. PATENT DOCUMENTS

| | | | | |
|---|---|---|---|---|
| 5,752,961 A | * | 5/1998 | Hill ................. | A61B 17/221 606/113 |
| 2005/0085808 A1 | * | 4/2005 | Nakao ............. | A61B 17/221 606/113 |
| 2007/0250070 A1 | * | 10/2007 | Nobis ............. | A61B 17/32056 606/113 |
| 2018/0193009 A1 | * | 7/2018 | Ranallo ........... | A61B 17/320016 |

FOREIGN PATENT DOCUMENTS

WO    WO-2008044615 A1  *  4/2008  ....... A61B 17/32056

* cited by examiner

*Primary Examiner* — Martin T Ton
(74) *Attorney, Agent, or Firm* — Christopher Paradies; Paradies Law P.A.

(57) ABSTRACT

An endoscopic snare net comprises a net engaging a loop, such as by weaving the loop through a mesh of the net, and a tube having a lumen through which the net and loop may be extended and withdrawn by a control wire. The loop has one or more corners or a collared, free-floating slip tether or both thereof, which prevent the net from sliding free of the loop as the loop is retracted into the lumen of the tube, even if the loop is over-extended beyond the end of the tube.

11 Claims, 2 Drawing Sheets

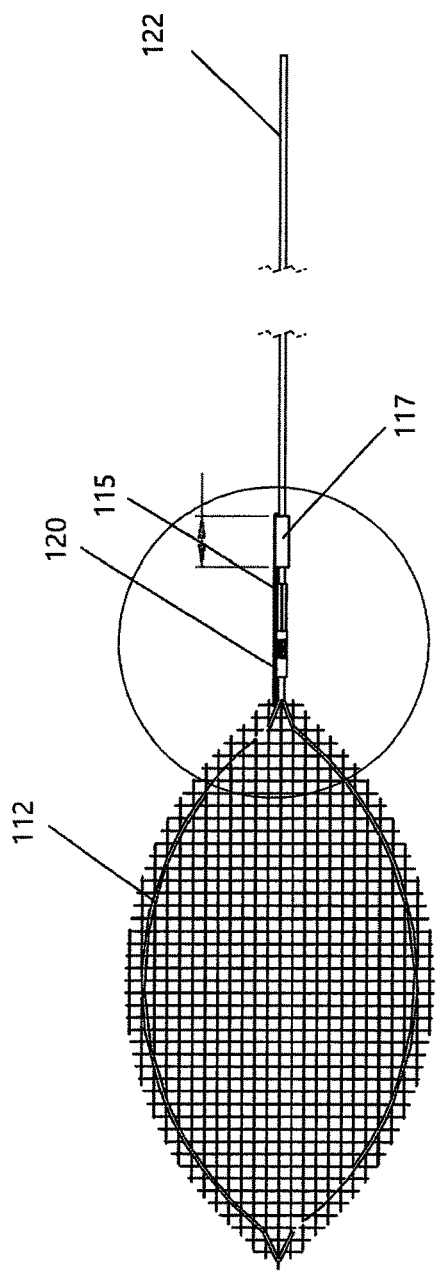
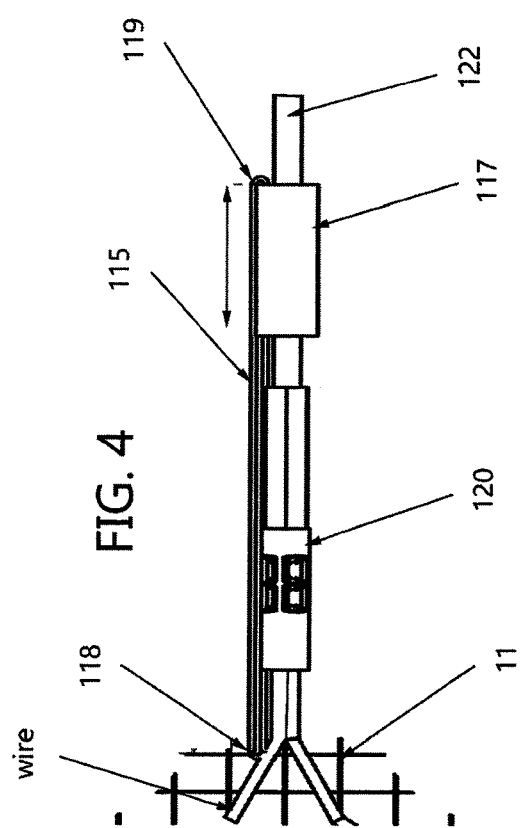
FIG. 3
FIG. 4

ENDOSCOPIC SNARE WITH ASYMMETRIC CORNERS

CROSS RELATED APPLICATIONS

This application is a continuation of U.S. patent application Ser. No. 16/630,099 filed Jan. 10, 2020 which is a 371 U.S. National Phase Appln. of PCT/US2018/041872 filed Jul. 12, 2018 which claims priority to U.S. Provisional Appln. No. 62/531,470, filed Jul. 12, 2017, which is incorporated by reference herein in its entirety.

FIELD OF THE INVENTION

The field relates to endoscopic devices, especially endoscopic snare nets.

BACKGROUND

Snare nets are known that tie a portion of the net to a cold loop or loops. Examples of known snare nets are found in U.S. Pat. Nos. 8,016,838; 7,618,437; 6,814,739; 5,906,621; 5,759,187; 5,486,182; 5,336,277; 5,201,740; and 5,190,542. However, all of these known snare nets have a difficult time forming a pocket for capturing a polyp or foreign object or have complex mechanisms or have excessive netting material that may snag or require a larger diameter lumen to pass through. While some of complex systems solve one or more of the problems, added complexity makes them potentially prone to failure and may add substantial cost to a medical procedure.

SUMMARY

An endoscopic snare net device comprises a shaped loop, a net and a tube having a lumen configured and arranged to accept the introduction of the loop and snare net through the lumen of the tube. The lumen is defined by a wall of a tube, such as a polymer tube. Herein, "lumen" means the open volume within a tube and is not limited to a biological lumen. The tube wall may have a collar disposed within the lumen, which may be fixed to the wall of a tube in a position at a distance from an end of the tube or may be free floating withing the tube around the control wire. The shaped loop may be made of a resilient, flexible material, such as metal. For example, the metal may be a steel, nitinol, titanium or alloys thereof. A distal end of the loop may be crimped and shaped to expand as the distal end exits the lumen first. One or more crimped corners may be disposed adjacent to the distal end of the loop.

In one example, the loop has one or more resilient bends in the proximal end of the loop that cause the loop to open and remain open, when the loop is extended fully from the tube. For example, a crimped corner is provided in addition to the one or more resilient bends that bias the loop to open when extended from the tube. In one example, the crimped corner is provided by bends in the loop, itself; however, the crimped corner serves a different purpose than the one or more resilient bends that bias the loop open. Instead of biasing the loop open, when the loop is extended from the tube, the crimped corner serves to secure a snare net during closing, which may be attached to the loop only by a single knot at the distal end of the loop, by weaving the loop through the openings in the net and/or by a tether looped through the net at a proximal end of the loop. In one example, a loop without at least one crimped corner results in the net riding forward on the loop as the loop is withdrawn into the tube. In contrast, a loop with at least one crimped corner pulls the net into the tube with the loop. In addition, a pair of crimped corners on opposite sides of the loop helped to form a distinct pocket within the net as the loop and net are pulled into the tube, as the loop closes. Even though the net is flat when the loop is fully deployed, as the loop is withdrawn, a pocket forms in the net that may be used to capture a foreign object while the loop closes around the foreign object.

In one example, the bends of the crimped corner do not form a loop (i.e. the crimped corner is open and does not loop around and cross over itself). Instead, in this example, the bends that form a crimped corner comprise a first bend in a first direction, a second bend in a second direction, and a third bend in a third direction. The first bend is nearer to the proximal end of the loop than the other bends. A bend in the loop creates an angle between the portion of the loop proceeding the bend and the portion of the loop after the bend. The first bend may bend the loop such that the first portion of the crimped corner is directed more inwardly, in a direction more toward an imaginary line extending from a central longitudinal axis of the tube, for example, when the loop is extended from the tube.

For example, a portion of the loop disposed before a first bend (i.e. closer to the proximal end of the snare loop), may be diverging outwardly from the imaginary line, when the loop is extended from the tube, and the first portion of the crimped corner after the first bend may extend less outwardly divergent, substantially parallel or inwardly divergent. Herein, "more outwardly divergent" means a greater angle, more away from the direction of the imaginary line extending from the central longitudinal axis of the tube, "more inwardly divergent" means a lesser angle, more toward the direction of the imaginary line extending from the same axis. In one example, the first bend changes the direction of the loop more inwardly divergent, the second bend changes the direction of the loop more outwardly divergent and the third bend changes the direction of the loop more inwardly divergent.

In one example, a more inwardly divergent first portion of the crimped corner is substantially parallel to the imaginary line, when the loop is extended from the tube. The term "substantially parallel" does not mean precisely parallel. Instead, the term "substantially parallel" means no greater than five degrees divergence, plus or minus, from parallel to an imaginary line extending from the central longitudinal axis of the tube. In an alternative example, the first portion is inwardly convergent (i.e. an imaginary line extending from the first portion eventually converges with the imaginary line extending from the central longitudinal axis of the tube, as both extend toward the distal end of the loop. In yet another example, the first portion of the crimped corner is outwardly divergent, but less so than the portion of the loop immediately preceding the first bend of the crimped corner.

In one example, a floating tether anchor is sized with an inner diameter that is greater than the outer diameter of a control wire passing through the inner diameter of the floating anchor, such that the floating anchor is not secured to the control wire and readily slides long the control wire within the tube. In one example, the outer diameter of a tether anchor is greater than the inner diameter of the tube surrounding the tether anchor, such that the tether anchor is secured in a fixed position relative to the tube. In an alternative example, a floating tether anchor has an outer diameter that is less than the inner diameter of the tube surrounding the tether anchor, such that the floating tether anchor freely slides or "floats" within the tube.

A method of using a snare net comprises extending a net engaged on snare loop from a lumen such that the loop opens; positioning the net and loop endoscopically to retrieve an object, such as a foreign object or polyp; withdrawing the net and loop at least partially back into the lumen, causing the loop to at least partially close and creating a pocket in the net, a crimped corner portion engaging a portion of the net near the proximal end of the loop, such that the net is pulled into the lumen by the crimped corner, when the loop is withdrawn into the lumen.

In one example, an endoscopic snare net device comprises a shaped loop having a distal end of the loop and a proximal end of the loop, the distal end of the loop being shaped to expand as the distal end of the loop exits the lumen first, and the proximal end of the loop having one or more corners existing the lumen after the distal end of the loop; a net; and a tube having a lumen configured and arranged to accept the introduction of the loop and snare net through the lumen of the tube, wherein the lumen is defined by a wall of the tube, and the net is engaged on the shaped loop such that the engaged loop is woven through holes in the net such that the net is retained on the shaped loop, the net being secured at the distal end of the shaped loop and, and the net engaging the one or more corners of the shaped loop at the proximal end of the shaped loop, the one or more corners being shaped such that the one or more corners retain the net from sliding forward on the shaped loop during extension of the shaped loop and net from the lumen and retraction of the shaped loop and net into the lumen.

For example, a shaped loop may be made of a resilient, flexible material, such as a metal, for example, a metal selected of a steel, nitinol, titanium or alloys thereof. In one example, a steel loop is used. The tube may have a collar disposed within the lumen, and the collar may fixed to the wall of the tube in a position at a distance from an end of the tube or may be free floating. Optionally, a tether may be coupled to the collar at a first end of the tether and to the net at a second end of the tether, opposite of the first end. The tube may have a free floating collar within the tube and disposed around a control wire coupled to the shaped loop. The tether may be coupled to the collar at a first end of the tether and to the net at a second end of the tether, opposite of the first end.

In one example, a length of the tether is selected such that the tether engages the net withdrawing the net into the tube, when proximal end of the shaped loop enters the tube during retraction of the shaped loop and net.

For example, one or more corners may be crimped and provide one or more resilient bends that bias the loop to open when extended from the lumen in addition to any bends that bias the loop open. The one or more corners secure a snare net on the loop during closing, and the net is secured to the distal end of the loop only by a single point of attachment at the distal end of the loop, for example. The one or more corners may comprise at least a first corner on a first side of the proximal end of the loop and a second corner on a second side of the proximal end of the loop, opposite of the first side such that a distinct pocket is formed within the net as the proximal end of the loop and the net are pulled into the tube, as the loop closes. The one or more corners may be open such that the loop does not extend over any other portion of the loop, i.e. the loop does not form a smaller loop by looping over itself.

Each of the one or more corners may comprise a first bend in a first bend angular direction, a second bend in a second bend angular direction, opposite of the first bend angular direction, and a third bend in a third bend angular direction opposite of the second bend angular direction, arranged such that each of the one or more corners extends outwardly from an imaginary line extending from a central longitudinal axis of the tube, when the loop is extended from the tube, for example. The first bend angular direction may be more inwardly divergent than the angular direction of an adjacent portion of the loop closer to the proximal end of the loop, the second bend angular direction may be more outwardly divergent than the first bend angular direction, and the third bend angular direction may be more inwardly divergent than the second bend angular direction, whereby an outwardly extending corner is formed at a outward vertex where the loop extending along the second bend angular direction diverges toward the third bend angular direction and an inwardly extending bend is formed at an inward vertex where the loop extending from the first bend angular direction diverges toward the second bend angular direction, for example. In one example, the one or more corners form at least one zig zag in a portion of the loop.

In one example, a loop anchor couples the loop to the control wire, wherein the collar is sized with an inner collar diameter that is greater than an outer wire diameter of the control wire, and the loop anchor has a loop anchor outer diameter greater than the inner collar diameter of the collar, such that the collar cannot slide past the loop anchor outer diameter.

In one example, a method of using the endoscopic snare net comprises extending the net and the loop from the lumen such that the loop opens; positioning the net and loop endoscopically to retrieve an object; withdrawing the net and loop at least partially back into the lumen, causing the loop to at least partially close and creating a pocket in the net, one or more of the corners engaging a portion of the net near the proximal end of the loop, such that the portion of the net is pulled into the lumen by the one or more corners, when the loop is withdrawn into the lumen.

BRIEF DESCRIPTION OF THE DRAWINGS

The following drawings are illustrative examples and do not further limit any claims that may eventually issue.

FIG. 3 illustrates another example of an endoscopic snare net.

FIG. 4 illustrates a detail view of a tether as used with any of the previous examples.

When the same reference characters are used, these labels refer to similar parts in the examples illustrated in the drawings.

DETAILED DESCRIPTION

Figure 1:
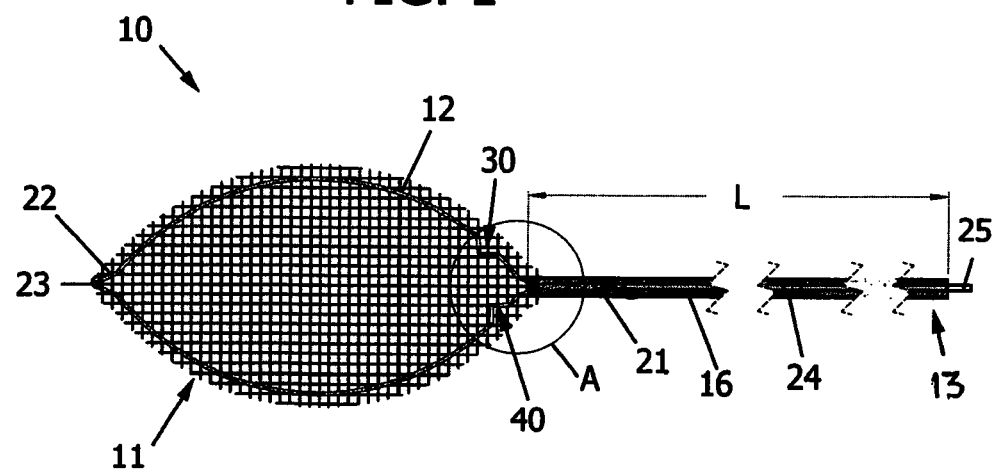
FIG. 1 illustrates an example of an endoscopic snare net.

FIG. 1 shows an example of an endoscopic snare net 10 comprises a net 11, a loop 12 and a tube 13. The tube 13 may comprise a lumen through which a cable 25 passes that may be used to extend and withdraw the net 11 and loop 12. The loop 12 may be a wire, which may be flat or round in cross section. The wire of the loop may pass through the net above and below the plane of the net weaving through the openings in the net. The net 11 is retained on the loop 12. A knot 23 may attach the net 11 to a distal end of the loop 22. For example, the distal end of the loop 22 may be crimped to provide a bias force that opens the loop 22 when the distal end 22 of the loop 22 is extended from the tube 13.

The cable 25 may be coupled to the loop 12 by a connector 21, such as crimped connector, such that moving the cable forward deploys the loop and net and withdrawing the cable 25 closes and retrieves the loop and net into the lumen of the tube 13. The cable and tube may be made any length L.

Figure 2:
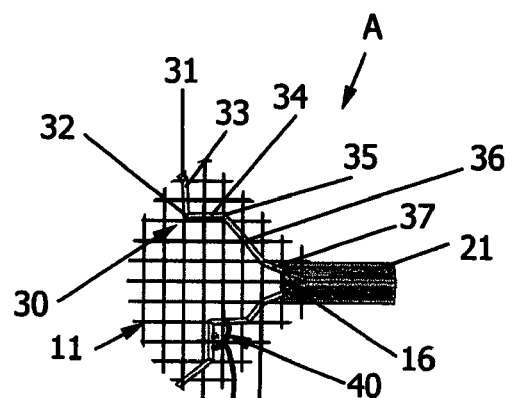
FIG. 2 illustrates a detail view (A) of the example of FIG. 1.

For example, a tether 16 may be coupled to a coupling 24 provided within the lumen of the tube 13 on one end of the tether 16, and the other end of the tether 16 may loop around a portion of the net 11 and/or the loop 12. In one example, the length of the tether is about the same as the distance from the distal tip of the loop to the proximal end of the loop extending out of the lumen when the loop is fully extended. The tether may loop around the net and the loop, preventing both from extended out of the lumen, completely, for example, as shown in more detail in the example of FIG. 2.

The example of FIG. 1 shows a plurality of crimped corners 30, 40. Additional crimped corners may be added. Alternatively, only a single crimped corner may be provided, for example. In testing, a pair of crimped corners 30, 40 created a pocket in the snare net 11 as the loop 12 is withdrawn into the lumen. The detail A in FIG. 1 is shown in more detail in the example of FIG. 2. A first divergent portion of the loop 37 extends from the lumen in this example, and a second divergent portion 36, after a bend in the loop 12, is more outwardly divergent than the first portion of the loop. A first crimped corner bend 35 causes a first portion 34 of the crimped corner to be directed less outwardly divergent. A second crimped corner bend 32 causes a second portion 33 of the crimped corner to be directed more outwardly divergent than any of the other portions. A third bend 31 causes a subsequent portion of the loop to be directed less outwardly divergent than the second portion 33 of the crimped corner 30, which continues in an arcuate oval shape until it nears the distal end 22 and knot 23.

Although not particular clear in the drawing, the location and angle of the portions of the crimped corners 30, 40 are not the same. In the crimped corner 30 the first corner portion 34 is substantially parallel; however, in the crimped corner 40 the first corner portion is more outwardly divergent and closer to the lumen opening of the tube 13. For example, the angle α between the first portion of the crimped corner 34 and the second portion of the crimped corner 33 may be greater than 90 degrees (or an obtuse angle), less than 90 degrees (or an acute angle) or substantially 90 degrees, where "substantially 90 degrees" means 90 degrees plus or minus 5 degrees, when the loop is fully extended from the lumen. In one example, an angle α is selected such that the angle prevents the net from sliding past the crimped corner 40, for example.

In another example, a tether 115 may be coupled with the snare net 11. For example, FIG. 3 shows an example of a loop 112 that does not have crimped corners, and FIG. 4 illustrates a detailed view of a tether as used on any of the previous examples. A tether 115 may be coupled with a net 11 by looping the tether through the net at a distal end 118 of the tether 115, and coupling the proximal end 119 of the tether 115 to a floating tether anchor 117 by looping the tether 115 through the anchor 117. The anchor 117 is referred to as a floating tether anchor, because the anchor 117 is not fixed to any other structure. The anchor is attached to neither the tube nor the wire 122. Instead, it slides or "floats" freely along the wire 122. One of the benefits of this floating anchor is that the tether 115 need not pull on the net 11 when the net is deployed, even if the net is over-deployed. This may prevent the net from being torn or unraveled by the tether. Instead, the tether floats on the wire 122 until the user withdraws the net and loop back into the tube. Then, the anchor 117 may be snagged by an obstacle, such as the end of the connecting cannula 120 or the like. Alternatively, a separate crimped cannula 121 may be crimped onto the control wire 122 and may act as the obstacle that engages the floating tether anchor 117. A space may be provided between the anchor 117 and any such obstacle to prevent snagging prior to withdrawal of the loop and net back into the lumen of a tube. In one example, a connecting cannula 120 may extend beyond the ends of the snare loop. As shown in FIG. 4, a connecting cannula 120 may be a crimped portion of a metal tube, which may be of the same material used in hypodermic needles or the like, for example.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

What is claimed is:

1. An endoscopic snare with asymmetric corners comprises:
   a tube having a distal end and a proximal end, a wall of the tube defining a lumen;
   a length of control wire extending through a portion of the lumen; and
   a shaped loop having a distal end of the loop and a proximal end of the loop, the distal end of the loop being shaped to expand as the distal end of the loop exits the distal end of the tube, and the proximal end of the loop being coupled with the length of control wire, the loop having at least two corners arranged such that the at least two corners exit the lumen after the distal end of the loop exits the tube and before the proximal end of the loop exits the tube, the at least two corners being comprised of at least a first corner on a first side of the loop and a second corner on a second side of the loop, the second side being opposite of the first side, and the second corner being closer to the proximal end of the loop than the first corner, such that the first side of the loop and the second side of the loop are asymmetric, and wherein each of the at least two corners comprises a first bend in a first bend angular direction, a second bend in a second bend angular direction, opposite of the first bend angular direction, and a third bend in a third bend angular direction opposite of the second bend angular direction, arranged such that each of the at least two corners extends outwardly from an imaginary line extending from a central longitudinal axis of the tube, when the loop is extended from the tube.

2. The endoscopic snare of claim 1, wherein the shaped loop may be made of a resilient, flexible material.

3. The endoscopic snare of claim 2, wherein the resilient, flexible material is a metal.

4. The endoscopic snare of claim 3, wherein the metal is of a steel, nitinol, titanium or alloys thereof.

5. The endoscopic snare of claim 3, wherein the metal is of a steel.

6. The endoscopic snare of claim 1, wherein one or more of the at least two corners are crimped and provide one or more resilient bends in addition to any bends that bias the loop open.

7. The endoscopic snare of claim 6, wherein the first bend angular direction is more inwardly divergent than the angular direction of an adjacent portion of the loop closer to the proximal end of the loop, the second bend angular direction is more outwardly divergent than the first bend angular direction, and the third bend angular direction is more inwardly divergent than the second bend angular direction, whereby an outwardly extending corner is formed at an outward vertex where the loop extending along the second bend angular direction diverges toward the third bend angular direction and an inwardly extending bend is formed at an inward vertex where the loop extending from the first bend angular direction diverges toward the second bend angular direction.

8. The endoscopic snare of claim 7, wherein the one or more of the at least two corners form at least one zig-zag in a portion of the loop.

9. The endoscopic snare of claim 8, wherein each of the at least two corners form at least one zig-zag in a portion of the loop.

10. The endoscopic snare of claim 9, further comprising a net having opposite sides, wherein the shaped loop is threaded through the opposite sides of the net such that each of the at least two corners retains a portion of the net at a location where the net engages each of the at least two corners, respectively.

11. A method of using the endoscopic snare of claim 1, comprising:
   extending the loop from the lumen such that the loop opens;
   positioning the loop endoscopically;
   withdrawing the loop at least partially back into the lumen, causing the loop to at least partially close with the first corner and the second corner causing an overlapping of at least a portion of the first side of the loop over the second side of the loop.

* * * * *